(12) United States Patent
Blackburn et al.

(10) Patent No.: US 10,034,736 B2
(45) Date of Patent: Jul. 31, 2018

(54) HERNIA REPAIR PATCH

(71) Applicant: C.R. Bard, Inc., Murray Hill, NJ (US)

(72) Inventors: Elizabeth Blackburn, Cranston, RI (US); Alexander Kirby Tee, Arlington, MA (US); Mariah Levitt, Boston, MA (US); Craig McCarthy, Beverly, MA (US); Aaron Abroff, Acton, MA (US); Evan Gant, Medford, MA (US)

(73) Assignee: C. R. Bard, Inc., Murray Hill, NJ (US)

( * ) Notice: Subject to any disclaimer, the term of this patent is extended or adjusted under 35 U.S.C. 154(b) by 134 days.

(21) Appl. No.: 14/636,514

(22) Filed: Mar. 3, 2015

(65) Prior Publication Data
US 2015/0250576 A1    Sep. 10, 2015

Related U.S. Application Data

(60) Provisional application No. 61/948,790, filed on Mar. 6, 2014.

(51) Int. Cl.
*A61F 2/00* (2006.01)
*A61F 2/02* (2006.01)
*A61B 17/00* (2006.01)

(52) U.S. Cl.
CPC ...... *A61F 2/0063* (2013.01); *A61B 17/00234* (2013.01); *A61F 2/0077* (2013.01); *A61F 2002/009* (2013.01); *A61F 2002/0072* (2013.01); *A61F 2002/0086* (2013.01); *A61F 2210/0004* (2013.01);
(Continued)

(58) Field of Classification Search
CPC ............ A61F 2/0063; A61F 2210/0076; A61F 2002/0072; A61F 2220/0033; A61F 2220/005; A61F 2220/0075; A61F 2230/0008; A61F 2230/0026; A61F 2250/0059; A61F 2250/0097; A61F 2210/0004; A61F 2210/0014; A61F 2210/00234; A61F 2/0077;
(Continued)

(56) References Cited

U.S. PATENT DOCUMENTS 460,940 A    10/1891   Baugh
5,116,357 A   5/1992   Eberbach
(Continued)

FOREIGN PATENT DOCUMENTS

EP    0557964 A1    9/1993
EP    1971275       8/2007
(Continued)

OTHER PUBLICATIONS

International Search Report from PCT/US2015/018496 dated Aug. 4, 2015.
(Continued)

*Primary Examiner* — Christopher L Templeton
*Assistant Examiner* — George J Ulsh
(74) *Attorney, Agent, or Firm* — Wolf, Greenfield & Sacks, P.C.

(57) ABSTRACT

A patch for repairing a hernia defect including a patch body that is reducible into a small configuration for delivery through a narrow incision or cannula into a patient. A support member assists in unfurling the patch body from the small configuration into an expanded configuration. A sleeve releasably mounts the support member to the patch body.

45 Claims, 7 Drawing Sheets

(52) U.S. Cl.
CPC .......... *A61F 2210/0014* (2013.01); *A61F 2210/0076* (2013.01); *A61F 2220/005* (2013.01); *A61F 2220/0033* (2013.01); *A61F 2220/0075* (2013.01); *A61F 2230/0008* (2013.01); *A61F 2230/0026* (2013.01); *A61F 2250/0059* (2013.01); *A61F 2250/0097* (2013.01)

(58) Field of Classification Search
CPC ........ A61F 2002/0086; A61F 2002/009; A61F 2002/0068
USPC ............................................... 606/151
See application file for complete search history.

(56) References Cited

U.S. PATENT DOCUMENTS

| | | | |
|---|---|---|---|
| 5,141,515 A | 8/1992 | Eberbach | |
| 5,147,374 A | 9/1992 | Fernandez | |
| 5,176,692 A | 1/1993 | Wilk et al. | |
| 5,258,000 A | 11/1993 | Gianturco | |
| 5,333,624 A | 8/1994 | Tovey | |
| 5,366,460 A | 11/1994 | Eberbach | |
| 5,368,602 A | 11/1994 | De la Torre | |
| 5,370,650 A | 12/1994 | Tovey et al. | |
| 5,395,383 A | 3/1995 | Adams et al. | |
| 5,397,332 A | 3/1995 | Kammerer et al. | |
| 5,405,360 A | 4/1995 | Tovey | |
| 5,634,931 A | 6/1997 | Kugel | |
| 5,797,960 A | 8/1998 | Stevens et al. | |
| 5,824,082 A | 10/1998 | Brown | |
| 5,916,225 A | 6/1999 | Kugel | |
| 5,919,232 A | 7/1999 | Chaffringeon et al. | |
| 5,957,939 A | 9/1999 | Heaven et al. | |
| 6,258,113 B1 | 6/2001 | Adams et al. | |
| 6,565,590 B2 | 5/2003 | Kieturakis et al. | |
| 6,575,988 B2 | 6/2003 | Rousseau | |
| 6,616,685 B2 | 9/2003 | Rousseau | |
| 6,702,827 B1 | 3/2004 | Lund et al. | |
| 6,911,037 B2 | 6/2005 | Gainor et al. | |
| 7,235,042 B2 | 6/2007 | Vanden Hoek et al. | |
| 7,273,489 B2 | 9/2007 | Boudjemline | |
| 7,377,936 B2 | 5/2008 | Gainor et al. | |
| 7,824,420 B2 | 11/2010 | Eldridge et al. | |
| 7,947,054 B2 | 5/2011 | Eldar et al. | |
| 8,388,633 B2 | 3/2013 | Rousseau et al. | |
| 8,500,762 B2 | 8/2013 | Sholev et al. | |
| 8,562,633 B2 | 10/2013 | Cully et al. | |
| 9,439,643 B2 | 9/2016 | Darois et al. | |
| 9,504,548 B2 | 11/2016 | Darois et al. | |
| 9,642,689 B2 | 5/2017 | Sholev et al. | |
| 2002/0103494 A1 | 8/2002 | Pacey | |
| 2002/0133236 A1 | 9/2002 | Rousseau | |
| 2004/0019360 A1 | 1/2004 | Farnsworth et al. | |
| 2004/0087980 A1 | 5/2004 | Ford et al. | |
| 2005/0049635 A1 | 3/2005 | Leiboff | |
| 2005/0171569 A1 | 8/2005 | Girard et al. | |
| 2006/0015143 A1* | 1/2006 | Alvarado | A61F 2/0063 606/213 |
| 2006/0247586 A1 | 11/2006 | Voegele et al. | |
| 2007/0066980 A1 | 3/2007 | Leahy | |
| 2007/0185506 A1 | 8/2007 | Jackson | |
| 2007/0260179 A1 | 11/2007 | Sholev et al. | |
| 2007/0265710 A1 | 11/2007 | Brown et al. | |
| 2008/0065229 A1 | 3/2008 | Adams | |
| 2008/0195121 A1 | 8/2008 | Eldar et al. | |
| 2009/0254103 A1 | 10/2009 | Deutsch | |
| 2009/0270999 A1 | 10/2009 | Brown | |
| 2010/0069947 A1 | 3/2010 | Sholev et al. | |
| 2010/0241145 A1 | 9/2010 | Cook | |
| 2010/0261953 A1 | 10/2010 | Townsend et al. | |
| 2010/0261954 A1 | 10/2010 | Townsend et al. | |
| 2010/0261956 A1 | 10/2010 | Townsend et al. | |
| 2010/0292718 A1 | 11/2010 | Sholev et al. | |
| 2011/0011407 A1 | 1/2011 | Townsend et al. | |
| 2011/0054500 A1 | 3/2011 | Levin et al. | |
| 2011/0112560 A1 | 5/2011 | Sholev | |
| 2011/0118706 A1 | 5/2011 | Gingras et al. | |
| 2011/0152897 A1 | 6/2011 | Bates | |
| 2011/0224704 A1 | 9/2011 | Bailly et al. | |
| 2011/0288567 A1 | 11/2011 | Ranucci et al. | |
| 2011/0295283 A1 | 12/2011 | Darois et al. | |
| 2012/0065649 A1 | 3/2012 | Towler | |
| 2013/0035704 A1 | 2/2013 | Dudai | |
| 2013/0060263 A1 | 3/2013 | Bailly et al. | |
| 2013/0103042 A1* | 4/2013 | Davis | A61B 17/00234 606/114 |
| 2013/0103058 A1 | 4/2013 | Gobran | |
| 2013/0178876 A1 | 7/2013 | Horton et al. | |
| 2013/0218178 A1 | 8/2013 | Shandas | |
| 2013/0218179 A1 | 8/2013 | Sholev et al. | |
| 2013/0231526 A1 | 9/2013 | Felix et al. | |
| 2013/0267970 A1 | 10/2013 | Cardinale et al. | |
| 2014/0025093 A1 | 1/2014 | Horton et al. | |
| 2014/0051915 A1 | 2/2014 | Sholev et al. | |
| 2014/0058416 A1 | 2/2014 | Brown | |
| 2014/0088343 A1* | 3/2014 | Arcand | A61L 27/16 600/30 |
| 2014/0088619 A1 | 3/2014 | Cardinale et al. | |
| 2014/0188250 A1* | 7/2014 | Fearnot | A61L 27/60 623/23.72 |
| 2015/0148824 A1 | 5/2015 | Horton et al. | |
| 2015/0157437 A1* | 6/2015 | Cohen | A61F 2/0063 606/151 |
| 2015/0209129 A1* | 7/2015 | Bailly | A61F 2/0063 606/151 |
| 2015/0257866 A1 | 9/2015 | Filipiak et al. | |
| 2016/0151136 A1 | 6/2016 | Hamilton et al. | |
| 2017/0100229 A1 | 4/2017 | Darois et al. | |
| 2017/0181831 A1 | 6/2017 | Felix et al. | |
| 2017/0181832 A1 | 6/2017 | Felix et al. | |
| 2017/0181833 A1 | 6/2017 | Felix et al. | |

FOREIGN PATENT DOCUMENTS

| | | |
|---|---|---|
| EP | 1336391 B1 | 12/2011 |
| FR | 2769825 | 4/1999 |
| WO | WO 13/007535 | 1/2003 |
| WO | WO 2003/002029 | 1/2003 |
| WO | WO 2007/087146 A2 | 8/2007 |
| WO | WO 2007/087146 A3 | 8/2007 |
| WO | WO 07/115110 | 10/2007 |
| WO | WO 2010/027898 | 3/2010 |
| WO | WO 2010/039249 | 4/2010 |
| WO | WO 2010/059234 | 5/2010 |
| WO | WO 11/137224 | 11/2011 |
| WO | WO 2012/047414 A1 | 4/2012 |
| WO | WO 2013/007534 A1 | 1/2013 |
| WO | WO 2013/048272 A1 | 4/2013 |
| WO | WO 2013/049791 A1 | 4/2013 |
| WO | WO 2013/049795 A1 | 4/2013 |
| WO | WO 2013/062933 A1 | 5/2013 |
| WO | WO 2013/142353 A1 | 9/2013 |
| WO | WO 13/148839 | 10/2013 |
| WO | WO 2013/148719 | 10/2013 |

OTHER PUBLICATIONS

International Preliminary Report on Patentability for International Application No. PCT/US2015/018496, dated Sep. 15, 2016, 12 pages.

* cited by examiner

HERNIA REPAIR PATCH

RELATED APPLICATIONS

This Application claims priority under 35 U.S.C. § 119(e) to U.S. Provisional Application Ser. No. 61/948,790, entitled "HERNIA REPAIR PATCH" filed on Mar. 6, 2014, which is herein incorporated by reference in its entirety.

FIELD

A patch for repairing a hernia.

BACKGROUND

A hernia defect is an opening or weakness in a tissue or muscle wall, such as the abdominal wall. One approach for repairing a hernia is to cover the tissue or muscle wall defect with a patch of repair fabric. The patch may be placed in an open procedure or through a minimally invasive procedure, such as by a laparoscopic technique. In a laparoscopic hernia repair, a patch is delivered through a narrow cannula to a treatment site within the patient. As the patch is much larger than the cannula bore, the patch must be reduced in size to enable passage through the small opening into the patient. After laparoscopic deployment, the patch needs to return to an enlarged shape sufficient to cover the defect. Certain hernia repair patches include a resilient support member, such as an elastic wire, that is collapsed along with the patch into a reduced configuration and delivered through the laparoscopic cannula. After exiting the cannula, the resilient support member unfurls causing the associated patch to expand into the enlarged repair configuration. The expanded patch including the resilient support member is then fixated to the tissue or muscle wall over the defect.

SUMMARY

According to one aspect, a patch for repairing a hernia defect includes a patch body having a periphery, a first axis and a second axis perpendicular to the first axis, the first axis and the second axis intersecting at approximately a center of the patch body. The patch body is configured to be manipulated into a reduced configuration for insertion through a narrow incision or cannula into a patient. A support member assists in unfurling the patch body from the reduced configuration to an expanded configuration. A mount, such as a sleeve, holds the support member, the mount being removably attached to the patch body.

According to another aspect, a patch for repairing a hernia defect includes a patch body having a periphery, a first axis and a second axis perpendicular to the first axis, the first axis and the second axis intersecting at approximately a center of the patch body. A support member has first and second opposed side portions that are intersected by the first axis. The patch body and the support member are configured to be manipulated together along the second axis into a reduced configuration for insertion through a slender incision or cannula into a patient. Each of the first and second opposed side portions of the support member include an abrupt inward deflection that reduces resistance to manipulation of the support member in the direction of the second axis.

According to another aspect, a patch for repairing a hernia includes a patch body having a first axis and a second axis perpendicular to the first axis. The patch body is configured to be manipulated along the second axis into a reduced configuration for insertion through a narrow incision or cannula into a patient. The patch body includes a second edge portion that is intersected by the second axis, with the second edge portion having a first thickness. A stop is positioned along the second edge portion, the stop having a second thickness greater than the first thickness. An introducer has a patch receiving opening sufficiently large to admit the second edge portion but not sufficiently large to admit the stop.

According to another aspect, a patch for repairing a hernia includes a patch body having a first axis and a second axis that is perpendicular to the first axis, the first axis and the second axis intersecting at approximately a center of the patch body. The patch body has a first shape and size when viewed along the first axis and a second shape and size when viewed along the second axis. The first shape and size is different from the second shape and size. The patch body has a first pair of edges that are intersected by the first axis and a second pair of edges that are intersected by the second axis. A tab extends outwardly from each of either the first pair of edges or the second pair of edges.

According to another aspect, a method of repairing a hernia includes positioning a hernia repair patch against a tissue or muscle wall including the hernia defect. The hernia repair patch includes a patch body and a mount, such as a sleeve, releasably attached to the patch body. The mount holds a support member that assists in unfurling the hernia repair patch from a reduced configuration into an expanded configuration. The patch body is fixed to the tissue or muscle wall. The mount holding the support member is detached from the patch body.

According to a still further aspect, a method of arranging a hernia repair patch for delivery into a patient includes positioning a hernia repair patch within a patch receiving area of an introducer. The hernia repair patch has an edge portion including a stop that is not passable through the patch receiving area. The stop is located on one side of the introducer and a second portion of the patch is located on another side of the introducer.

BRIEF DESCRIPTION OF DRAWINGS

Aspects of the invention are described below with reference to the following drawings in which like numerals reference like elements, and wherein.

DETAILED DESCRIPTION

Figure 1:
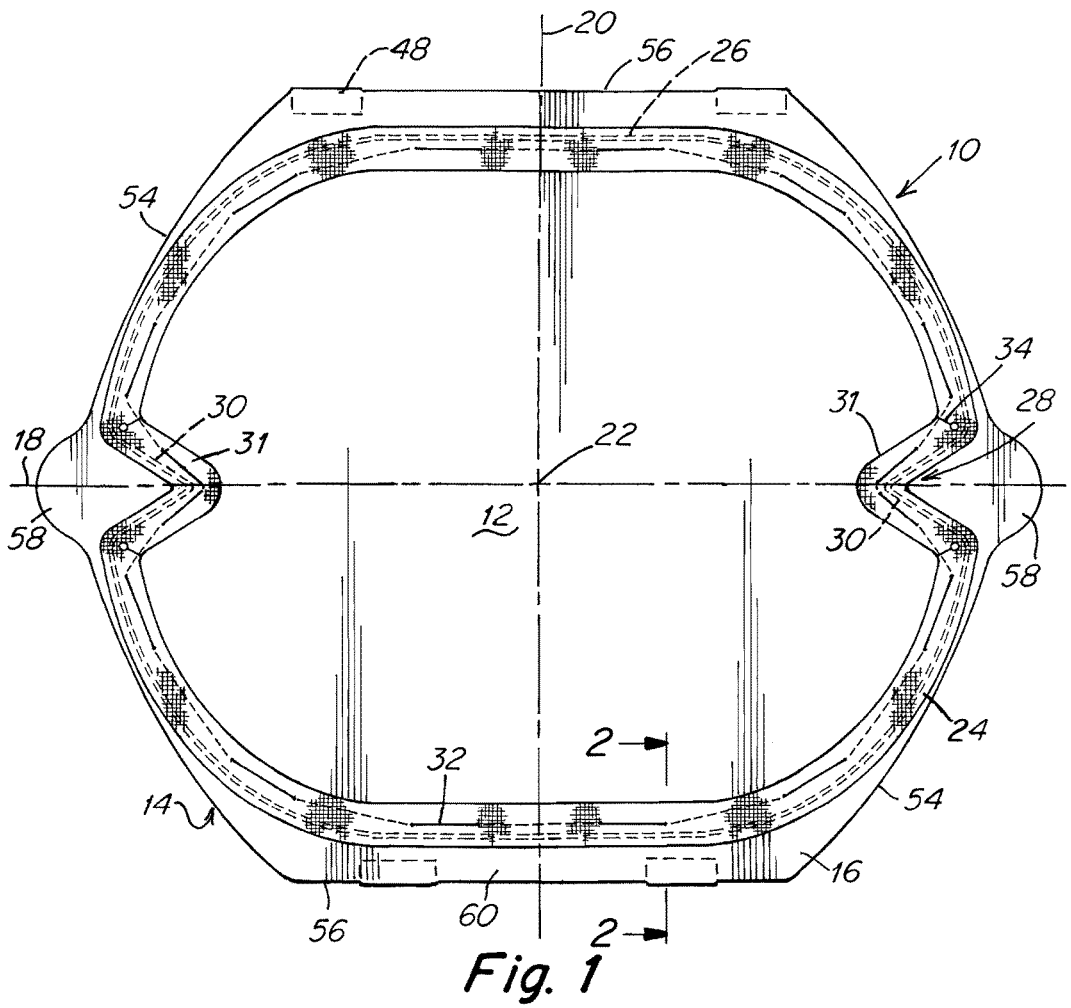
FIG. 1 is an illustration of a hernia repair patch.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with the repair of a hernia, specifically a ventral hernia. However, the invention is not necessarily so limited, and may be employed to repair other types of hernias, other soft tissue or muscle wall defects, as well as may be used in other surgical or medical treatments. With respect to repair of a ventral hernia, the repair patch may be placed in the intraperitoneal, preperitoneal, retromuscular, or other anatomical space, as the invention is not so limited. For ease of understanding, the hernia repair patch is described in connection with a laparoscopic procedure but may be employed in other minimally invasive procedures, in an open procedure, or in other techniques for repairing a hernia or other soft tissue defect as should be apparent to one of skill in the art.

A patch for repairing a hernia may include a patch body having a first side that will be positioned against a tissue or muscle wall, such as the abdominal wall, that includes the defect. The first side of the patch body may be configured for tissue ingrowth. Where the patch will be located adjacent sensitive organs, such as the intestines or other viscera, an opposite side of the patch body may include a barrier, such as a layer of barrier material or a barrier coating, to prevent adhesions between the first side of the patch and the sensitive organs.

In a minimally invasive technique, as well as in certain open procedures, a hernia repair patch may be reduced in size to facilitate delivery of the prosthetic device to the treatment site. For example, in a laparoscopic procedure, a hernia repair patch may be rolled into a slender cylindrical shape, or otherwise collapsed into a smaller configuration, suitable for passage through a narrow cannula which may have an inner diameter of approximately 10 mm, of approximately 5 mm, or even a finer size. To assist in unfurling the patch into an expanded shape after deployment through a cannula, a support member may be integrated with a patch body. The support member may have a resiliency or other property (e.g., shape memory) that allows the support member to deform from an initial, expanded, shape into a compact configuration as the patch is reduced in size for laparoscopic delivery, and then return to the initial shape, or at least to a shape larger than the reduced shape, upon exiting the cannula. Recovery of the support member causes the attached patch to spread out into an expanded configuration. For example, and without limitation, the support member may be rollable into a reduced size for delivery through the laparoscopic cannula to the hernia repair site. A representative support member may be formed from a nitinol wire. The support member may have a frame-like shape and may generally follow the periphery of the patch. Representative shapes of a support member include circular, oval or a polygon. The support member may be configured with one or more deforming force reducers that reduce resistance of the support member to being rolled up. For example, and without limitation, such a deforming force reducer may include at least one abrupt, inward bend or jog of the support member.

After deployment through the laparoscopic cannula, and unfurling of the support member, the expanded patch body may be located against the abdominal wall and fixated in place. For example, sutures, tacks, and/or staples, may be applied through a border region, and/or at other locations, of the patch into healthy tissue surrounding the defect. With the patch body spread out over the hernia defect, and secured to the tissue or muscle wall, the inventors have recognized that there no longer is need for the support member. Accordingly, the support member may be releasably attached to the hernia repair patch, allowing selective removal of the support member by the surgical team after expanding, positioning, and/or fixation of the patch body.

In one embodiment, the support member may be associated with a mount that is removably attached to the patch body. For example, and without limitation, the support member may be contained in a sleeve, such as a flat sleeve (e.g., sheath), that is releasably attached to the patch body. Detachment of the sleeve will, in turn, separate the support member contained within the sleeve, from the patch body. The detached support member may then be removed from the patient, such as by withdrawing the sleeve and associated support member through the same narrow opening in which the patch had been delivered into the patient. The deforming force reducers may reduce the resistance of the support member to forming a shape conducive to passing back out through the smaller minimally invasive access opening in response to a withdrawal force. The sleeve containing the support member may be configured with one or more reliefs to allow the support member to bend, twist, and/or otherwise deform in response to the pulling or other removal force.

Figure 2:
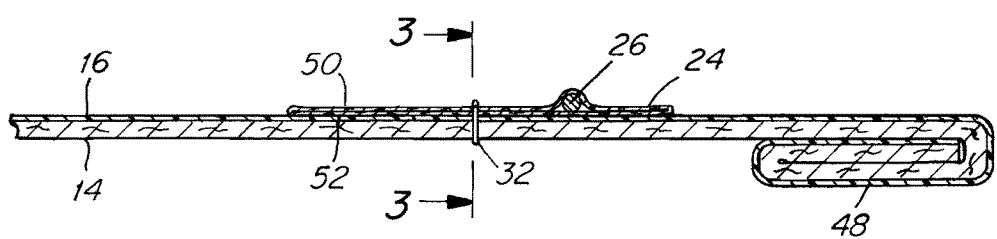
FIG. 2 is a sectional illustration along lines 2-2 of FIG. 1.
Figure 3:
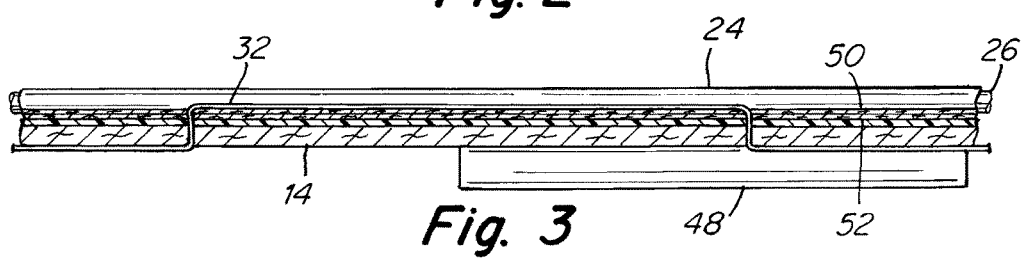
FIG. 3 is a sectional illustration along lines 3-3 of FIG. 2.

As shown in FIGS. 1-3, a hernia repair patch 10 may include a patch body 12 having a first surface 14 that is arranged for tissue ingrowth and a second surface 16 that is configured as a barrier to adhesions between the first surface and sensitive organs or tissue, such as the intestines or other viscera. The first surface may include a tissue infiltratable layer such as a mesh or other porous fabric amenable to tissue ingrowth, and the second surface may be a solid or substantially non-porous barrier layer or a barrier coating that will prevent contact between the viscera and the porous tissue ingrowth fabric. The patch body may be defined by a first axis 18 and a second axis 20 that is substantially perpendicular to the first axis. The intersection of the first and second axes may coincide with a center, or approximate center 22, of the patch body. Alternative arrangements of a patch body are contemplated as should be apparent to one of skill in the art. For example, and without limitation, the patch body may include only a tissue infiltratable layer, only a solid or non-tissue infiltratable layer, or a combination of tissue infiltratable and non-tissue infiltratable aspects situated in the same layer.

A sleeve 24 may be located on the second surface and may extend generally around the periphery of the patch body as illustrated in FIG. 1. The sleeve may have a reduced profile and may, for example and without limitation, be in the form of a flat sleeve so as to minimize the overall thickness of the patch when reduced for delivery through a narrow opening to the treatment site. The sleeve may be a continuous component or may include two or more discrete segments that are contiguous and/or spaced from each other which in combination form the sleeve.

Contained within the sleeve is a support member 26, such as an elastic wire, that will assist in unfurling the patch body into an expanded shape after laparoscopic delivery to the treatment site. The support member may be formed of nitinol, other super-elastic metals, appropriately resilient metals, plastics or other materials, other shape memory metals or plastics, and comparable materials as should be apparent to one of skill in the art. To reduce the patch into a slender configuration suitable for delivery through a laparoscopic cannula, the patch may be rolled up into a cylinder. For example, and without limitation, the patch may be rolled along the second axis. The support member may have a frame-like configuration, and may generally follow the periphery of the patch body.

A frame-type support member, such as a support member shaped as a circle or oval that is integrated with the patch body, may resist being rolled up into a tight cylinder. Accordingly, the support member may be configured with one or more deforming force reducers 28 that assists in mitigating resistance to rolling up of the support member. A deforming force reducer may be in the shape of an inward deflection or jog of the support member. A support member configured with a deforming force reducer will allow the patch to more readily be reduced in size and to form a more compact roll. The deforming force reducer may be configured as a V-shaped bend 30, as illustrated, or other inward relief, although other arrangements of a deforming force reducer that reduce resistance to rolling of the support member are contemplated as should be apparent to one of skill in the art. The deforming force reducer may coincide with a first axis 18 of the patch body, and a pair of deforming force reducers may be located on opposite side portions of the support member. Alternatively, a deforming force reducer may be provided at additional, or other, locations along the support member. In certain embodiments, a deforming force reducer is provided along one or more segments of the support member that most closely parallel the axis along which the patch is to be manipulated along into a reduced configuration. Without wishing to be bound by any theory, such one or more segments are believed to have considerable resistance to being reduced in size about itself (e.g., rolled into a cylindrical form). The deforming force reducer, for example a V-shaped bend of the support member, may have a length between ends of the deforming force reducer extending in the direction of the second axis, that is 15-50% of the length of a side of the patch body in the direction of the second axis. The sleeve containing the support member may be configured to accommodate the deforming force reducers. As illustrated, the sleeve may include a pair of V-shaped bends 31 similar to the two V-shaped inflections of the support member.

The sleeve may be releasably attached to the patch body. For example, and without limitation, a continuous suture 32 may run between the sleeve, or other support member mount, and the patch body. The continuous suture can be cut at one or more locations and then the sleeve pulled away from the patch body until the sleeve fully detaches. Alternatively, the suture may be sufficiently weak or be modified to include one or more localized weak points that will fail upon application of a sufficient pulling force. The suture may be arranged to extend primarily on the first surface of the patch body, to limit the amount of suture remaining on the second surface that faces the viscera after detachment of the sleeve. Further, the suture may be a monofilament to reduce the likelihood of adhesion formation; although it is contemplated that a multifilament suture may be employed as well. The suture may be resorbable, so that segments of the continuous suture remaining with the patch body after removal of the sleeve are degraded over time by the body. Other approaches for releasably attaching the sleeve to the patch body are contemplated. For example, and without limitation, the sleeve may be adhered by a relatively weak adhesive to the patch body. Another option is to configure the sleeve and/or patch body so as to releasably engage each other. In one such arrangement, the patch body may include one or more slits that releasably receive an aspect of the sleeve. In another arrangement, the sleeve may include a slight lip that projects over an edge of the patch to engage the first surface. The lip will provisionally hold the sleeve to the patch body, but will give way in response to a sufficient pulling force allowing the sleeve to detach from the patch body.

After detachment from the patch body, the expanded sleeve and support member may be removed through the same narrow opening along which the patch, in collapsed form, was delivered into the patient. However, the support member is now in an expanded configuration much larger than the narrow cannula and may have an inherent resistance, due to its circular or oval shape, to being drawn through such a narrow passageway. The deforming force reducer of the support member, such as the V-shaped inward bends 30 previously described, may facilitate deformation of the support member into a shape that is passable through the cannula or other narrow passage when the support member is subject to pulling, or other withdrawal, force. Slits 34 or other reliefs may be provided in the sleeve containing the support member to make it easier for the support member to bend, twist, or otherwise deform into a tighter configuration as it is drawn through the narrow cannula opening. Such slits or other reliefs may be provided anywhere along the length of the sleeve. As shown, the sleeve reliefs may be provided at the location of the V-shaped inflection of the support member within the sleeve. The reliefs in the sleeve also allow the support member to flex when a pulling force is applied to the sleeve to detach the sleeve from the continuous suture engagement with the patch body.

Figure 4:
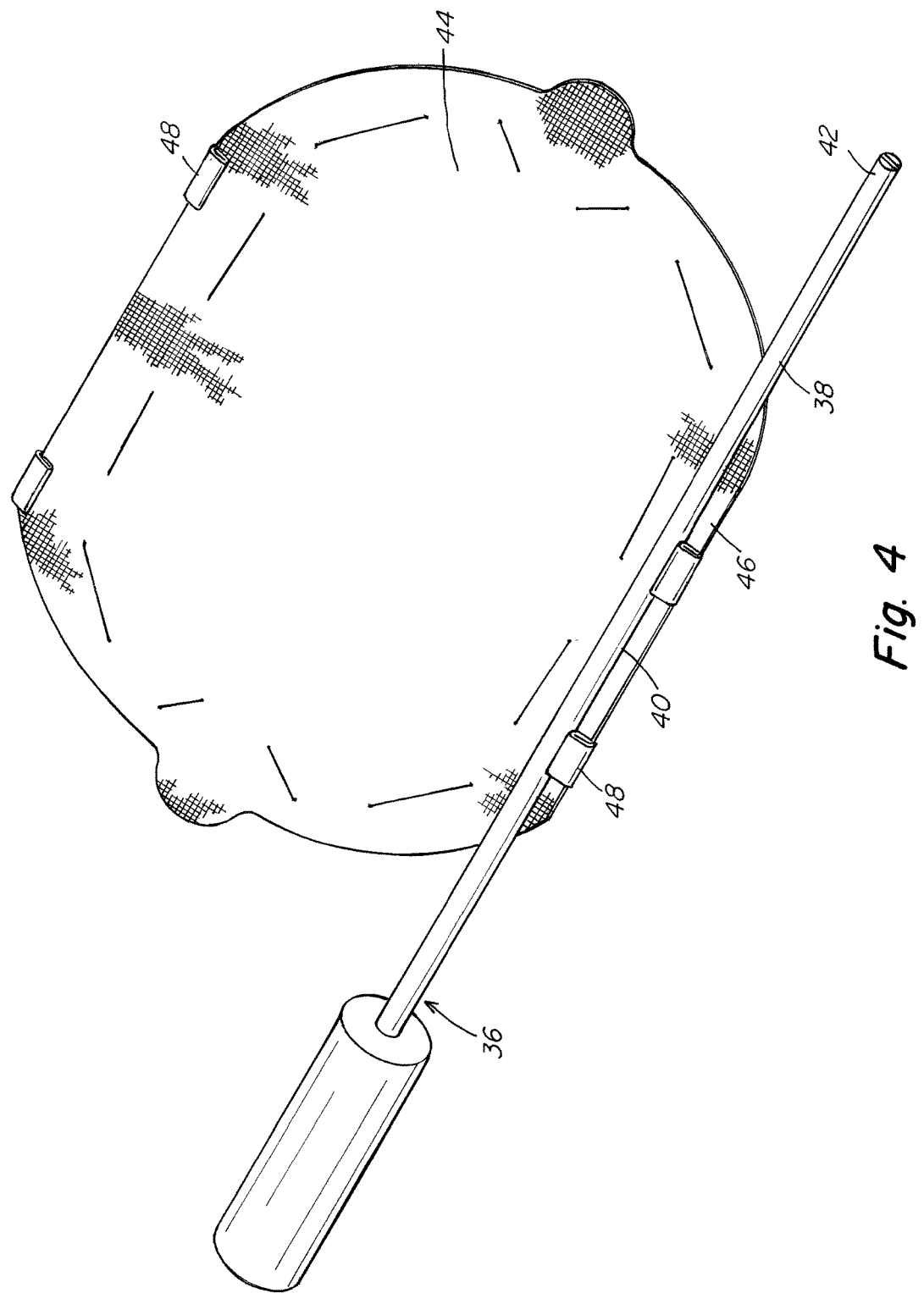
FIG. 4 is an illustration of a hernia repair patch associated with an introducer.
Figure 5:
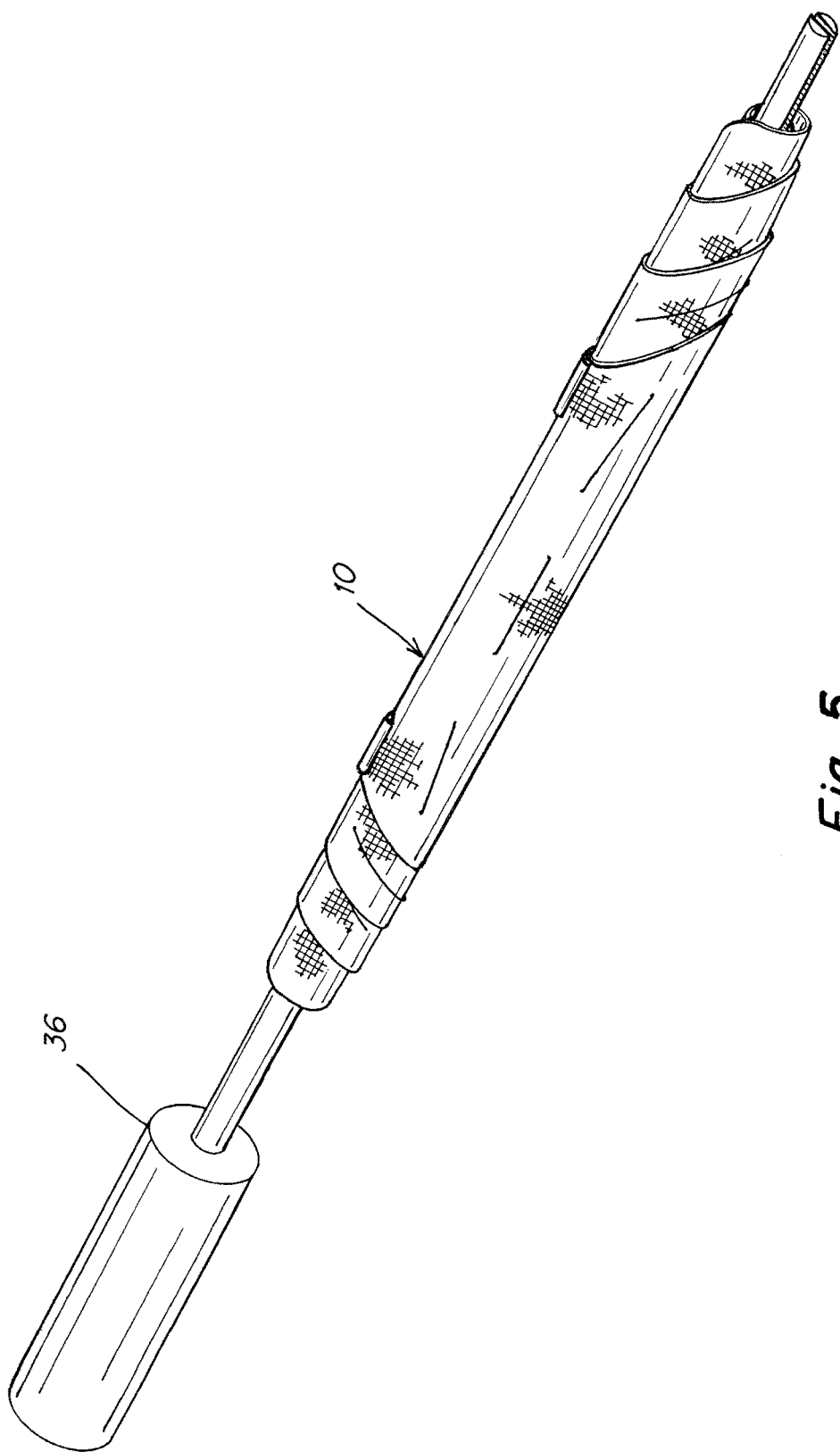
FIG. 5 is an illustration of a hernia repair patch reduced in size about an introducer shaft.

Various techniques may be employed to reduce a patch to a smaller configuration suitable for delivery through a narrow opening, such as via a laparoscopic cannula. In one embodiment shown in FIGS. 4-5, an introducer 36 includes a shaft 38 having a patch receiving area 40 that may be defined, for example, between splined sections 42 of the shaft. The patch receiving area may threadably receive the patch as shown in FIG. 4. A major portion 44 of the patch may be located on one side of the shaft, with an edge portion 46 of the patch including a stop 48 that is positioned on the other side of the shaft. The patch body has a first thickness that is receivable within the patch receiving area of the introducer while the stop has a second thickness, greater than the first thickness, which is too large to be admitted through an opening into the patch receiving area. Rotating the shaft will cause the patch to roll up about the shaft in the area of the patch receiving area, as shown in FIG. 5. The stop prevents the edge portion of the patch from slipping back out of the introducer as the stop is too large to pass into the patch receiving area. The stop may be provided along a portion of an edge of the patch, if not along the entire portion.

In certain embodiments, a stop may include two or more nubs spaced along an edge portion of the patch. The stop may be formed of a same material included in the patch body or of a different material. In one embodiment, the stop is formed of one or more layers of a tissue infiltratable fabric including, but not limited to, the same tissue infiltratable fabric, if such is employed, in the first surface of the patch body. The one or more layers may be separately formed and then attached to the patch body. For example, and without limitation, one or more fabric pieces may be stacked up at the edge portion, or a fabric winding may be located at the edge portion. In another embodiment, the stop is located in a notch or gap in an edge portion of the patch body. In a still further embodiment, the stop may be provided on the sleeve, or other support member mount, so that the stop is removed along with the detachable sleeve after fixation of the patch;

there being no functional requirement for the stop after the patch has been reduced in size and delivered to the treatment site.

The stop may be formed integral with the patch body or sleeve, or may be a separate component that is attached to the patch body or sleeve such as by stitching, bonding, fusing, or other connecting approach as should be apparent to one of skill in the art. A stop may be provided on opposite sides of the patch or only on one side of the patch. Where a stop is provided on opposite edges of the patch, the respective stops may be axially offset so as not to overlie each other when the patch is rolled up and, consequently, such an offset arrangement of the stops reduces the overall profile of the rolled-up patch.

In some embodiments, the sleeve may be in the form of a flat sleeve or sheath having a bottom layer 52 and a top layer 50, and at least one of the top and bottom layers may have a substantially flat shape. In one embodiment, the bottom layer that is attached to the patch body, such as to the second surface, may have a flat shape, with the top layer having a curved profile. In other embodiments, a wall may be located between the long edges of the top and bottom layers. As shown in FIG. 2, the top and bottom layers may be substantially in contact, separated only where the support member is sandwiched therebetween, providing a reduced profile. The sleeve may be formed of a nylon material, other synthetic polymers, as well as natural materials.

The patch body may have any form appropriate for repairing a hernia defect. The patch may be substantially flat or may be arranged with a concave, convex, or a combination concave/convex surface. As illustrated, the patch body may be substantially planar and have a first axis and a second axis that is perpendicular to the first axis, with an intersection of the first axis and the second axis that may coincide with a center of the patch. The distance between edges of the patch body along the first axis may be greater than the distance between edges of the patch body along the second axis; that is, the patch body may be elongated along the first axis. The shape of the patch body when viewed along the first axis may be different than the shape of the patch body when viewed along the second axis. For example, and without limitation, the edges of the patch body intersected by the first axis may be generally round 54 while the edges of the patch body intersected by the second axis may be linear 56 and run parallel to the first axis. Without wishing to be bound by any theory, the linear edges provide a greater area for threading to the introducer as compared to a patch body having round edges—such as if the patch were circular or oval shaped. One or more stops may be provided at either, or both, of the linear edge portions. Other patch body configurations are contemplated as should be apparent to one of skill in the art.

A particular orientation of the patch relative to the defect may be desirable for a particular treatment. Accordingly, the patch may include various markings or other indicia that allow the surgical team to position the patch in a desired orientation. For example, and without limitation, a pair of short tabs 58 may project from the edges of the longer side of the patch body. As illustrated, the tabs may have a round or lobe shape, although other shapes are contemplated as should be apparent to one of skill in the art. Each of the tabs may have a length, measured in a side-to-side direction parallel with the axis that separates the patch edges from which the tabs project, that is a percentage of the distance between the edges of the patch body. It is contemplated that the tabs may have a length from between 1-20%, 1-15%, 1-10%, 1-5%, and 1-2.5%, of such distance between the respective patch body edges from which the tabs project. The tabs may have a length, measured in a direction parallel with the axis separating the edges from which the tabs project, of 5-15 mm, 7.5-12 mm, or 8-10 mm.

In certain embodiments, and as illustrated, each of the tabs may coincide with one of the patch body axes 18, 20. However, one or both tabs may be arranged off-axis. Although a single tab is shown projecting from each of the edges of the long sides of the patch body, a different number of tabs may project from one edge as compared to the other and either edge (or both edges) may include two or more tabs. Further, it is contemplated employing a single tab extending only from one edge of the patch body. As an alternative, or in addition, to the tabs, the patch may include other markings or indicia that signal the orientation of the patch. For example, and without limitation, the patch may include high contrast markings that provide visual guidance to the surgical team regarding a rotational or other orientation of the patch. The high contrast markings may be provided on the first surface, second surface, sleeve or other aspects of the patch.

In certain embodiments, portions 60 of the first and second surfaces may extend outwardly beyond the sleeve. Such extensions of the first and second surfaces may provide locations for applying sutures, tacks, staples, or other fixation elements through the patch. In other embodiments, the first and second surfaces do not project outwardly of the sleeve, or only project a negligible amount that is insufficient to receive a fixation element to secure the patch. In the embodiment illustrated, the first and second surfaces extend beyond the sleeve a greater amount along the edges intersected by the second axis as compared to the first axis. In other embodiments, the first and second surfaces extend a greater amount outside of the sleeve along the edges that are intersected by the first axis. In still other embodiments, a comparable amount of the first and second surfaces extends beyond the sleeve along all edges of the patch.

The patch body may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of permanent material, resorbable material, or a combination of permanent and resorbable materials. It should be appreciated that the patch body may be formed of any biologically compatible material, synthetic or natural, suitable for repairing a tissue or muscle wall defect as would be apparent to one of skill in the art.

A representative embodiment of the hernia repair patch and a representative procedure for using same is now described. A hernia repair patch configured to repair a ventral hernia includes a patch body having a tissue infiltratable layer on one side and a barrier layer on the other side. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. Another option is to embed the polypropylene knit into a film of SEPRA (bioresorbable hydrogel barrier). The polypropylene side would face the abdominal wall and the ePTFE or SEPRA side would face the viscera. A pair of tabs extend outwardly from sides of the patch body. A flat nylon sheath is attached by a single, continuous suture to the patch body, and generally follows the periphery of the patch body. Contained within the flat sheath is a 0.020 inch diameter nitinol wire that also generally follows the periphery of the patch body. At opposed sides of the patch, the flat sheath and superelastic wire deflect inwardly. Portions of the sheath at or near the inward deflection may include slits or other features that allow the sheath to fold in response to a pulling force.

Figure 6:
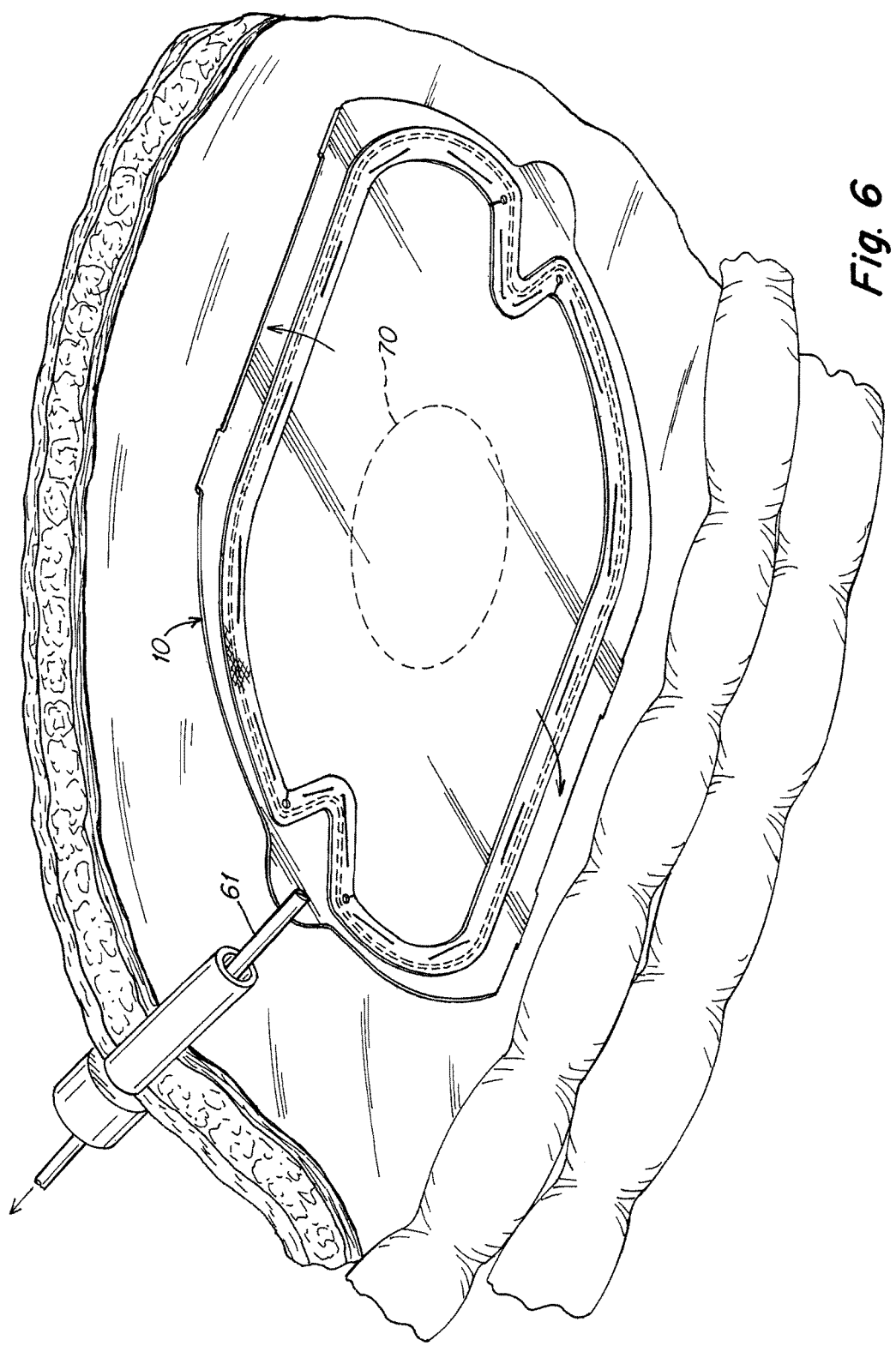
FIG. 6 is an illustration showing a hernia repair patch after laparoscopic delivery and being positioned against an abdominal wall.
Figure 7:
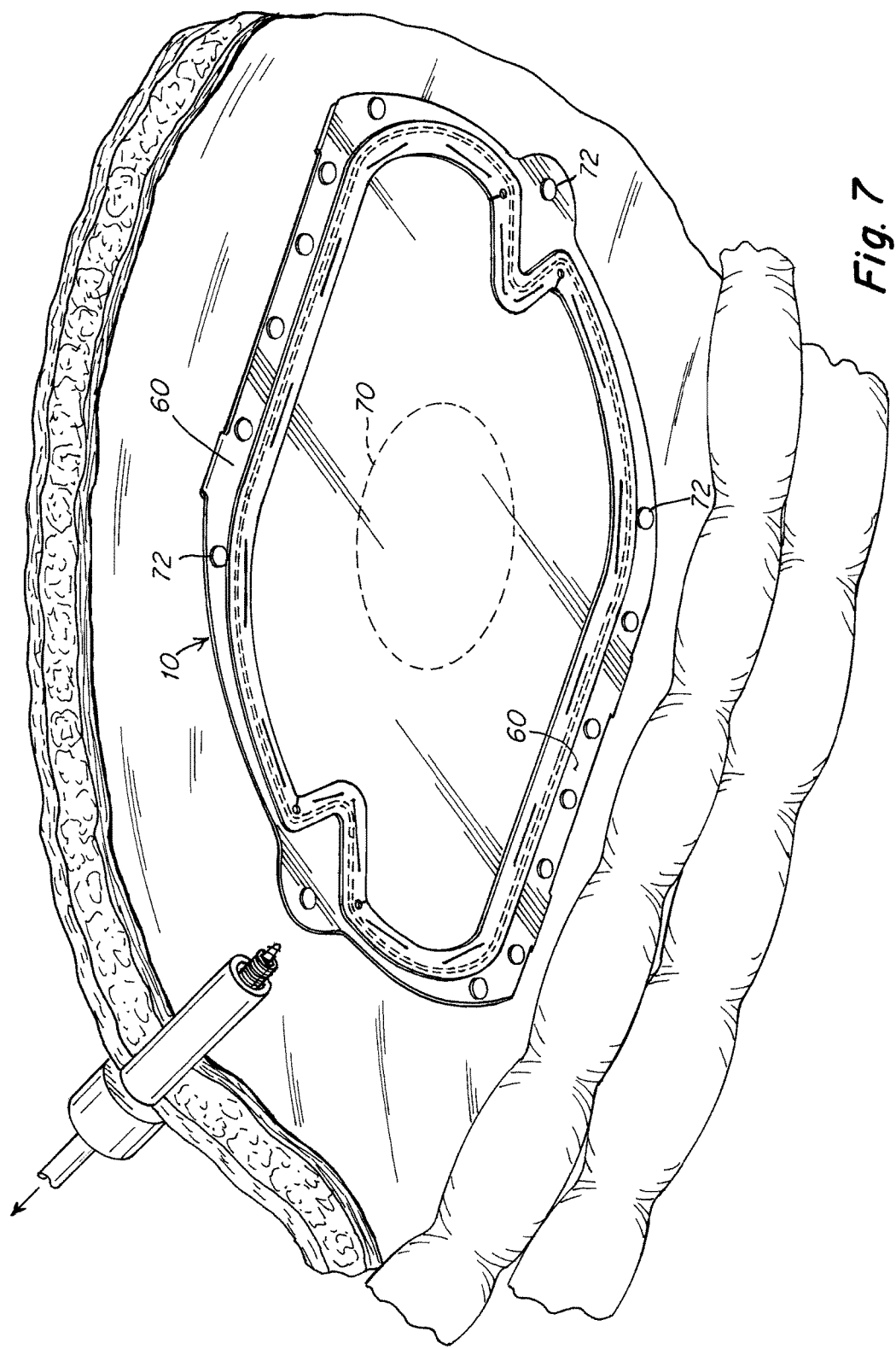
FIG. 7 is an illustration of a hernia repair patch being fixated to an abdominal wall.
Figure 8:
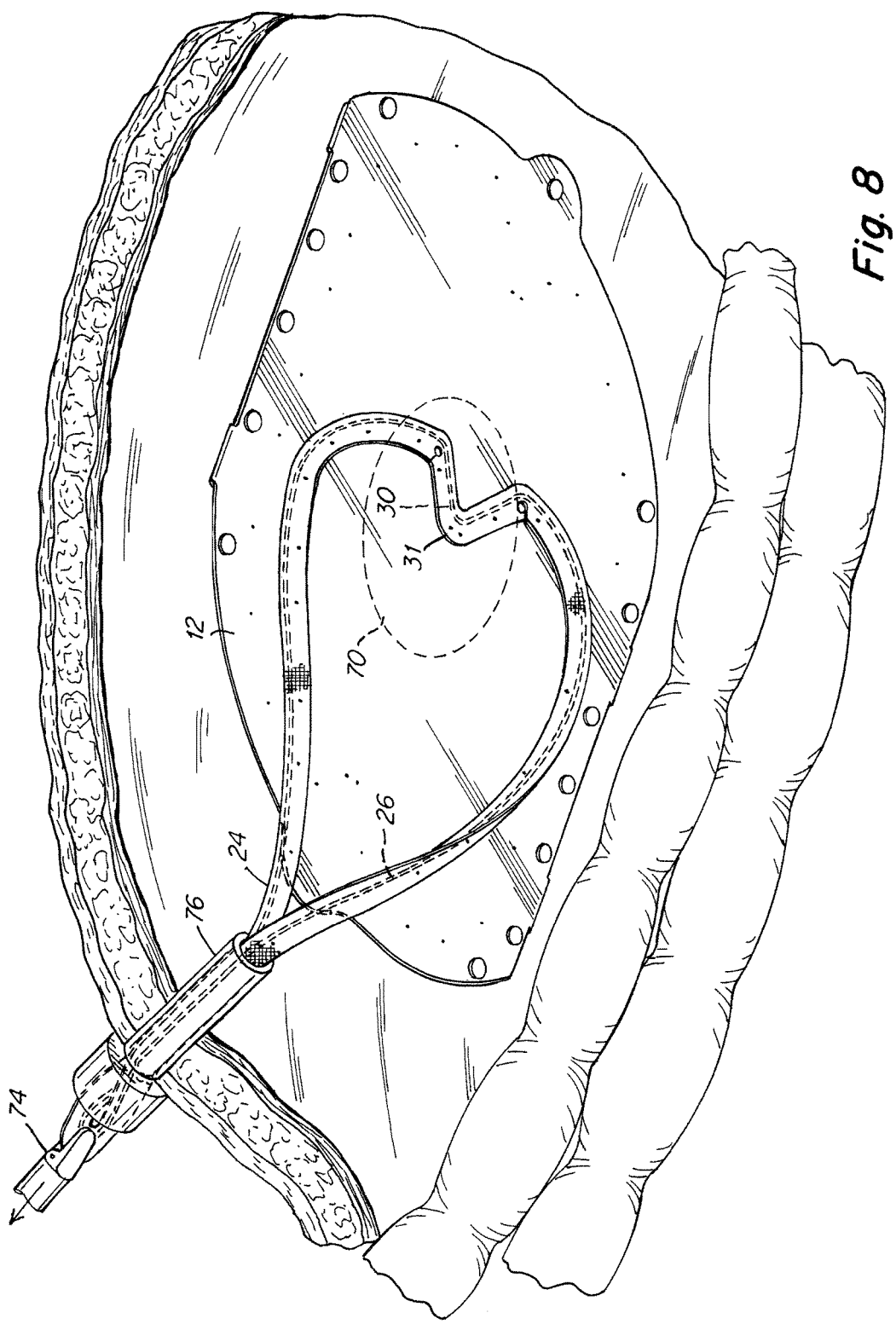
FIG. 8 is an illustration of a detached sleeve containing a support member being removed from the treatment site.
Figure 9:
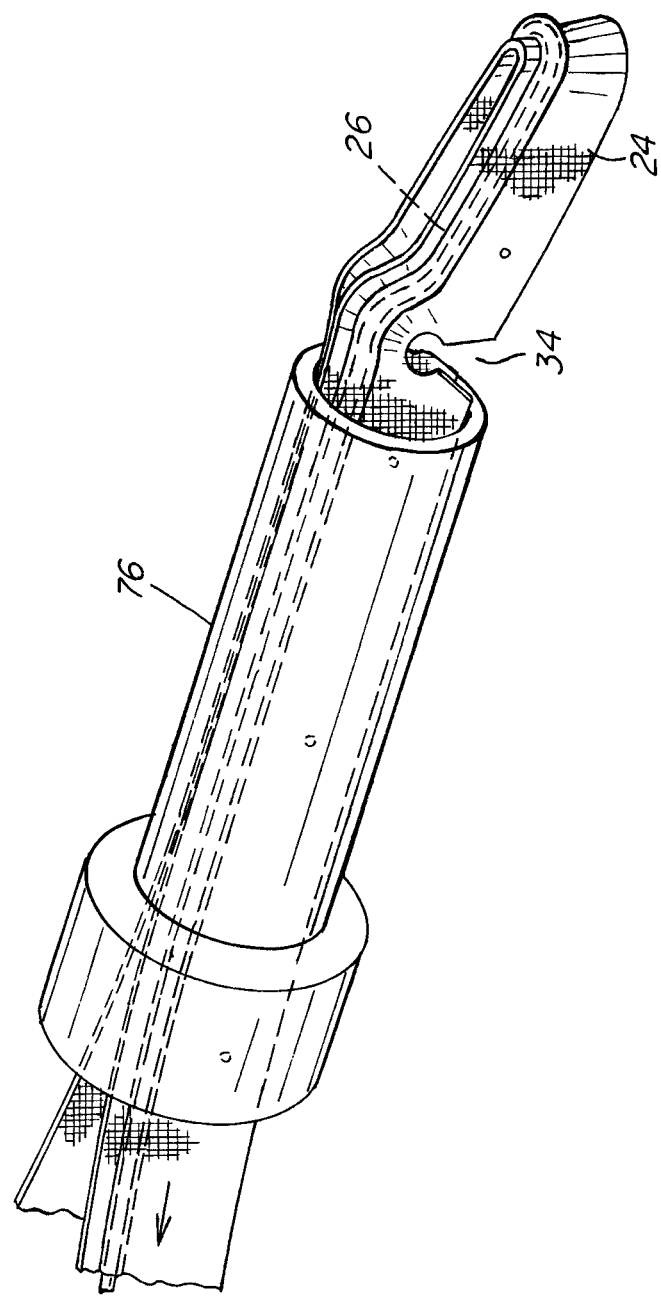
FIG. 9 is an illustration of a detached sleeve and support member being drawn through a cannula.

The patch is rolled along an axis of the patch into a small configuration, as illustrated in FIG. 5, and then delivered through a narrow incision or cannula into a patient. Upon exiting the incision or cannula, the nitinol wire springs back to a larger shape, spreading the patch body into an expanded configuration. A laparoscopic tool 61 as shown in FIG. 6, or a suture extending from the patch, may be manipulated to position the enlarged patch against the abdominal wall, covering the defect 70. A fixation element 72, such as a suture, tack, or staple, is applied through the respective anchoring tabs to provisionally secure the patch in place. Additional fixation elements 72 are then applied, such as through the periphery of the patch extending outwardly beyond the sheath, as shown in FIG. 7. The flat sheath is then detached from the anchored patch. For example, as illustrated in FIG. 8, the surgical team may use a grasper 74 or other laparoscopic instrument to grip the sheath and then to pull and tear the sheath away from the patch. The flat sleeve and contained nitinol wire may bend or fold at the respective inward deflections in response to the pulling force, helping to detach the sleeve from the patch body. Slits and other deforming force reducers in the sheath facilitate bending of the sheath and nitinol wire. The detached sleeve and nitinol wire may then be pulled by the grasper or other laparoscopic instrument through the cannula 76, as shown in FIG. 9. The V-shaped jogs or other force deforming reducers may facilitate collapse or twisting of the nitinol wire into a compact shape that will fit through the narrow laparoscopic passageway as the support member and sleeve are pulled by the laparoscopic instruments through the cannula.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A patch for repairing a hernia, comprising:
  a patch body having a periphery, a first axis and a second axis perpendicular to the first axis, the first axis and the second axis intersecting at approximately a center of the patch body, the patch body configured to be manipulated into a reduced configuration for insertion through a narrow incision or cannula into a patient;
  a support member to assist unfurling the patch body from the reduced configuration to an expanded configuration; and
  a mount that holds the support member, the mount including a sleeve that contains the support member, the sleeve being removably attached to the patch body, the support member being contained by the sleeve when the sleeve is detached from the patch body.

2. The hernia repair patch of claim 1, wherein the sleeve is a flat sleeve.

3. The hernia repair patch of claim 1, wherein the mount is removably attached to the patch body with a continuous suture.

4. The hernia repair patch of claim 1, wherein the support member includes at least one abrupt inward deflection.

5. The hernia repair patch of claim 4, wherein the at least one abrupt inward deflection is located along the first axis or the second axis.

6. The hernia repair patch of claim 4, wherein the at least one abrupt inward deflection has a V-shape.

7. The hernia repair patch of claim 4, wherein the at least one abrupt inward deflection includes a pair of abrupt inward deflections, each of the abrupt inward deflections located along one of the first axis and the second axis.

8. The hernia repair patch of claim 1, wherein the sleeve includes one or more reliefs configured to facilitate bending of the sleeve and the contained support member in response to a pulling force applied to the sleeve.

9. The hernia repair patch of claim 8, wherein the support member includes at least one inward deflection and the sleeve includes at least one relief adjacent the at least one inward deflection.

10. The hernia repair patch of claim 8, wherein the patch body includes a first surface configured to allow tissue ingrowth and a second surface configured to inhibit the formation of adhesions.

11. The hernia repair patch of claim 1, wherein the sleeve generally follows the periphery of the patch body.

12. The hernia repair patch of claim 1, wherein the support member extends generally about the periphery of the patch body.

13. A patch for repairing a hernia, comprising:
  a patch body having a periphery, a first axis and a second axis perpendicular to the first axis, the first axis and the second axis intersecting at approximately a center of the patch body;
  a frame-shaped support member contained within and generally following the periphery of the patch body, the support member having first and second opposed side portions that are intersected by the first axis, the patch body and the support member configured to be manipulated together along the second axis into a reduced configuration for insertion through a slender incision or cannula into a patient, the support member including a single pair of abrupt inward deflections, each of the first and second opposed side portions of the support member including one of the pair of abrupt inward deflections along a segment thereof that reduces resistance to manipulation of the support member in the direction of the second axis; wherein the frame-shaped support member is held by a mount releasably attached to the patch body.

14. The hernia repair patch of claim 13, wherein each of the abrupt inward deflections is located along the first axis.

15. The hernia repair patch of claim 13, wherein each of the abrupt inward deflections has a V-shape.

16. The hernia repair patch of claim 13, wherein the support member has a substantially oval or circular shape.

17. The hernia repair patch of claim 13, wherein the opposed side portions bow outwardly away from the second axis.

18. The hernia repair patch of claim 13, wherein each of the opposed side portions has a first end and a second end and a length between the first and second ends measured in a direction of the second axis, and each of the abrupt inward deflections has a first end and a second end and a length between the first end and second ends measured in the direction of the second axis, the length of each of the abrupt inward deflections ranging from 15-50% of the length of the opposed side portions.

19. The hernia repair patch of claim 13, wherein the mount includes a sleeve.

20. The hernia repair patch of claim 13, wherein the support member has a ring-like configuration.

21. The hernia repair patch of claim 20, wherein the support member has a circular, oval or polygonal shape.

22. The hernia repair patch of claim 13, wherein each of the first and second opposed side portions has outwardly curved segments extending from opposite ends of the abrupt inward deflection.

23. A patch for repairing a hernia, comprising:
a patch body having a first axis and a second axis perpendicular to the first axis, wherein the patch body is configured to be manipulated along the second axis into a reduced configuration for insertion through a narrow incision or cannula into a patient;
the patch body including an outer periphery with a second edge portion that is intersected by the second axis, the second edge portion having a first thickness;
a stop positioned along the second edge portion, the stop having a second thickness greater than the first thickness; and
an introducer having a patch receiving opening sufficiently large to admit the second edge portion but not sufficiently large to admit the stop.

24. The hernia repair patch of claim 23, wherein the patch body includes a tissue ingrowth side and a barrier side, and the stop extends outwardly from the tissue ingrowth side.

25. The hernia repair patch of claim 24, wherein the tissue ingrowth side includes a tissue infiltratable fabric and the barrier side includes a barrier layer or a barrier coating.

26. The hernia repair patch of claim 23, wherein the stop is formed of a tissue infiltratable fabric.

27. The hernia repair patch of claim 26, wherein the stop includes a plurality of layers of tissue of infiltratable fabric.

28. The hernia repair patch of claim 26, wherein the stop includes a cylinder of tissue infiltratable fabric.

29. The hernia repair patch of claim 23, wherein the patch body includes a pair of opposed second edge portions, a first stop is positioned at one of the opposed second edge portions and a second stop is positioned at the other of the opposed second edge portion, wherein the first stop and the second stop are offset in the direction of the second axis so as not to overlie one another when the patch body is manipulated along the second axis into a reduced configuration.

30. The hernia repair patch of claim 23, further including a sleeve containing a support member, at least a portion of the sleeve extending along the second edge portion, wherein the stop is located on the portion of the sleeve extending along the second edge portion.

31. The hernia repair patch of claim 23, wherein the introducer includes a shaft having a pair of splined sections, the patch receiving area defined between the pair of splined sections.

32. The hernia repair patch of claim 31, wherein the pair of splined sections are resilient and spreadable apart to receive the patch body.

33. The hernia repair patch of claim 23, wherein the second edge portion includes an outermost edge of the patch body and adjacent areas of the patch body extending inwardly from the outermost edge.

34. A patch for repairing a hernia, comprising:
a patch body having a first axis and a second axis, wherein the second axis is perpendicular to the first axis, the first axis and the second axis intersecting at approximately a center of the patch body, the patch body including a layer of mesh fabric;
the patch body being planar and having a first shape and size when viewed along the first axis and a second shape and size when viewed along the second axis, the first shape and size being different from the second shape and size, the patch body having a first pair of edges that are intersected by the first axis and a second pair of edges that are intersected by the second axis;
a tab extending outwardly from each of either the first pair of edges or the second pair of edges;
wherein the patch body is configured to be manipulated into a reduced configuration for insertion through a narrow incision or cannula into a patient, and further including a support member to assist in unfurling the patch body from the reduced configuration to an expanded configuration; the patch body further including a mount that holds the support member, the mount being removably attached to the patch body.

35. The hernia repair patch of claim 34, wherein at least one of the tabs is positioned so that it intersects with either the first axis or the second axis.

36. The hernia repair patch of claim 35, wherein both of the tabs are positioned so that they each intersect with either the first axis or the second axis.

37. The hernia repair patch of claim 34, wherein the tab is in the shape of a lobe.

38. The hernia repair patch of claim 34, wherein the first pair of edges have a generally curved configuration, and the second pair of edges have a generally straight configuration.

39. The hernia repair patch of claim 38, wherein at least one of the first pair of edges has a first end and a second end and a first edge length between the first end and the second end, and at least one of the second pair of edges has a first end and a second end and a second edge length between the first end and the second end, and wherein the first edge length is greater than the second edge length.

40. The hernia repair patch of claim 39, wherein both of the first pair of edges has the same first edge length and both of the second pair of edges has the same second edge length.

41. The hernia repair patch of claim 34, wherein the patch body is elongated along the first axis.

42. The hernia repair patch of claim 34, wherein each tab is defined by a length measured outwardly from the side edge from which it extends and in a direction parallel to either the first axis or the second axis, the length of each tab ranging from 1-20% of a length, measured in the same axial direction, extending between the opposed edges from which each tab outwardly extends.

43. The hernia repair patch of claim 42, wherein each tab is defined by a length ranging from 1-5% of the length extending between the opposed edges from which each tab outwardly extends.

44. The hernia repair patch of claim 34, wherein each tab is defined by a length measured outwardly from the side edge from which it extends and in a direction parallel to either the first axis or the second axis, the length ranging from 8-10 mm.

45. The hernia repair patch of claim 34, wherein the mount includes a sleeve that contains the support member.

\* \* \* \* \*